United States Patent
Volker

(10) Patent No.: US 9,527,051 B2
(45) Date of Patent: Dec. 27, 2016

(54) MIXING DEVICE FOR PRODUCING READY-TO-USE MEDICAL FLUSH SOLUTIONS, PARTICULARLY FOR HEMODIALYSIS CONCENTRATES

(71) Applicant: Manfred Volker, Blankenbach (DE)

(72) Inventor: Manfred Volker, Blankenbach (DE)

( * ) Notice: Subject to any disclaimer, the term of this patent is extended or adjusted under 35 U.S.C. 154(b) by 291 days.

(21) Appl. No.: 13/787,944

(22) Filed: Mar. 7, 2013

(65) Prior Publication Data
US 2013/0235691 A1 Sep. 12, 2013

(30) Foreign Application Priority Data
Mar. 10, 2012 (DE) .................. 10 2012 004 886

(51) Int. Cl.
| | | |
|---|---|---|
| B01F 15/00 | (2006.01) | |
| A61M 1/16 | (2006.01) | |
| B01F 5/04 | (2006.01) | |
| B01F 5/10 | (2006.01) | |
| B01F 1/00 | (2006.01) | |

(52) U.S. Cl.
CPC ...... *B01F 15/00331* (2013.01); *A61M 1/1656* (2013.01); *A61M 1/1666* (2014.02); *B01F 1/0022* (2013.01); *B01F 1/0038* (2013.01); *B01F 5/0413* (2013.01); *B01F 5/106* (2013.01); *B01F 15/00032* (2013.01)

(58) Field of Classification Search
CPC .................................................. B01F 15/00331
USPC ........................................ 366/136, 137, 163.2
See application file for complete search history.

(56) References Cited

U.S. PATENT DOCUMENTS

| | | | | |
|---|---|---|---|---|
| 1,160,848 | A | * | 11/1915 | Conklin .................... 422/281 |
| 1,647,473 | A | * | 11/1927 | Rushmore ................ 239/304 |
| 4,202,760 | A | * | 5/1980 | Storey ............... A61M 1/1656 137/101.11 |
| 4,863,277 | A | * | 9/1989 | Neal et al. .................. 366/137 |
| 5,762,416 | A | * | 6/1998 | LeSire ....................... 366/136 |
| 7,264,730 | B2 | * | 9/2007 | Connell .............. A61M 1/16 210/138 |
| 2002/0057625 | A1 | * | 5/2002 | Russell et al. ............. 366/136 |

\* cited by examiner

*Primary Examiner* — David Sorkin
(74) *Attorney, Agent, or Firm* — Hammer & Associates, P.C.

(57) ABSTRACT

The mixing device for producing ready-for-use medical flush solutions, particularly for hemodialysis concentrates, comprising a source of ultrapure water which is connected via a supply line to a recirculation circuit in which a pump is disposed, comprising a computer and comprising a secondary-mixture connection line which is connectable to a feedstock container which prior to the beginning of the mixing operation contains powdery and/or granulated and/or slurried feedstocks that are to be mixed with the ultrapure water, is characterized in that a mixing venturi tube with its convergence chamber and its divergence chamber and a mixing valve are disposed in the recirculation circuit in flow direction one after the other.

8 Claims, 4 Drawing Sheets

Figure 1:
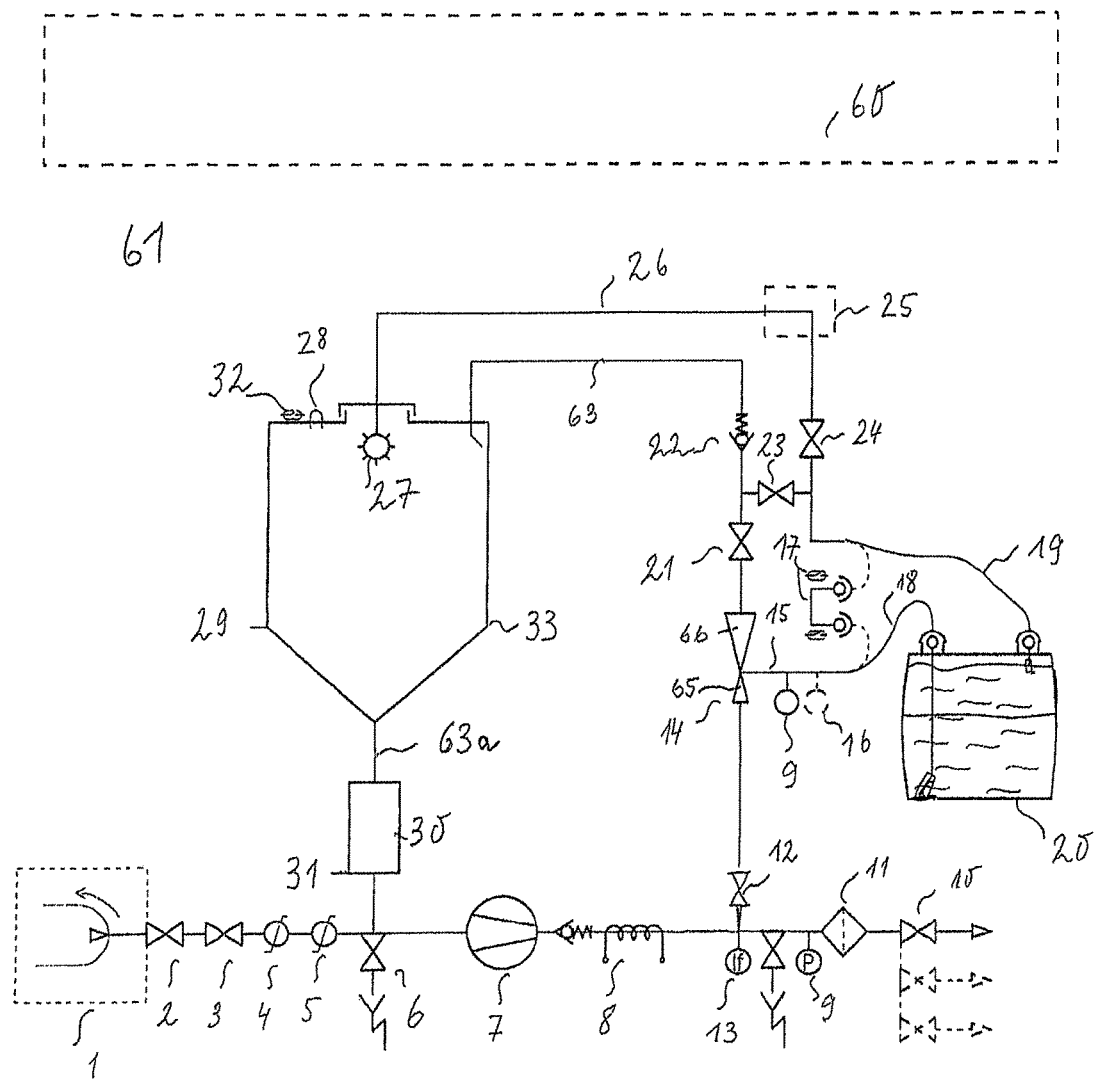

MIXING DEVICE FOR PRODUCING READY-TO-USE MEDICAL FLUSH SOLUTIONS, PARTICULARLY FOR HEMODIALYSIS CONCENTRATES

The subject matter of the invention is a technologically simple mixing device for producing ready-to-use medical flush solutions, particularly concentrates for hemodialysis.

Drawbacks of the prior art are:

The production is time-consuming; high energy consumption; dissolution of the feedstock takes a very long time.

The observation of normative specifications for finished solutions is rendered difficult because of an inaccurate dilution or liquid metering, respectively.

That is why troublesome in-house controls are required for accuracy.

Mixing unit and liquid are contaminated because of inadequate microbiological prevention; troublesome hygienic measures are needed.

The finished solution containers are without any visual accessibility with respect to the necessary level; there is no control with respect to the orientation of the tank; there is no long-term stability in plastic tanks.

Not all of the feedstock variants, e.g. powdery, granulated, slurried (pasty), can be processed. It is not possible to refill the feedstock container in situ.

A transfer of the finished solution to the place of use is not intended.

The following improvements are aimed at with the invention:

The mixing method should be
short, energy-saving;
normative specifications without in-house control should be observed for the finished solutions;
hygienically perfect;
technically simple.

This is accomplished by way of a failsafe, very precise metering of the liquid.

By way of a high hygiene/sterility, such as e.g. by very good flushing and possibly disinfecting possibilities.

The used components, such as finished solution container, can be equipped with a visual position and level detection and a calibratable level detection by means of sensors.

The feedstock container may be fitted to be refillable and may be filled with powdery, granulated or slurried (pasty) feedstock in situ.

The finished solution can be conveyed by way of a simple transfer to the place of use.

The improvements are accomplished in the following way:

The mixing device contains a computer with input and output units, a main mixing line and recirculation circuit, respectively, with a circulation pump, a venturi pump (venturi tube), and at least one valve and a secondary mixing line which branches off with a connection from the suction line of the venturi tube and is connected to the filled feedstock container and terminates with the other connection from the feedstock container via a further valve upstream into the main mixing line again.

The liquid needed for dilution or preparation is supplied from a source of liquid, which preferably in its central function consists of a reverse osmosis, by means of a precise metering device, which will be described hereinafter, to a preparation tank or finished solution container.

At the beginning of the mixing operation the main mixing line is first shut off by means of the main mixing valve and the liquid is conveyed in flow direction of the main mixing line via the secondary mixing line.

With advantage there is the possibility of operating main mixture and secondary mixture at the same time in such a manner that the secondary mixture is operated in countercurrent fashion with respect to the main mixture. To this end a further flow resistor is inserted upstream into the main mixing line such that the liquid is supplied to the feedstock container from above and is sucked off at the bottom by means of venturi pump.

With alternating countercurrent and co-current mixing through the feedstock container together with the operation of the main mixture at the same time—on condition that the liquid is flowing in countercurrent fashion through the feedstock container, a fast, inexpensive, efficient preparation of concentrate for the hemodialysis or medical flush solutions for other applications can be produced.

Downstream of the feedstock container, a flush line is connected, and no liquid can flow through said line in the connected state of the feedstock container. The flush line is advantageously completed at its end with a spray head and thereby terminates in the finished solution container such that the inner surface of the finished solution container can be cleaned almost completely and disinfected in case of need. The feedstock container can be aerated through the flush line.

To improve hygiene and to restore purity after a mixing operation, or after a long period without any operation, a physical or chemical disinfection device may be provided downstream of the flush line after the coupling place.

Entry of dangerous disinfectants during the mixing operation is thus not possible.

To ensure a residue-free emptying of the finished solution container, the mixing unit may be connected to a free outlet.

An essential component of the mixing device is the failure-monitored metering device. This device monitors the volume of the supplied liquid needed for the preparation of the feedstock; it is also decisive for accuracy, i.e. the suitability for use of the solution, and when validated feedstocks are used, it makes another time-consuming and cost-intensive checking of the finished solution superfluous.

In its basic configuration the metering device consists of a water inlet valve, an outflow valve, at least two level sensors for determining the supplied volume; the level sensor that is installed upstream is here simultaneously monitoring the tightness of the water inlet valve.

The finished solution container which is normally made of plastics is advantageously provided with a surrounding marking through which both the necessary liquid level(s) and an inclined position of the tank can be monitored by the user.

The second level sensor needed for determining the fill level or the volume is positioned inside this marking. For instance, these are optical, capacitive or other measuring sensors suited for detecting liquid.

Moreover, the sensor system can be used for other functions, such as e.g. also detection of the empty state of the tank.

Since, especially in plastic tanks, volume changes cannot be ruled out because of assembly, manufacture, load and ageing variations, the sensors located in the tank are adjustable in their position.

Moreover, a clamping belt may be attached in the center of the tank for preventing the frequently occurring tank bulge, said belt being prevented from slipping by knobs provided on the tank.

Another kind of metering device which can be used independently of the tank and also for variable inflow amounts consists in the basic configuration of a measuring chamber with e.g. at least one optical, capacitive or other measuring sensor which is suited for detecting liquid, and at least one connected flow meter and at least one valve.

Owing to the use of a measuring chamber, different finished solution containers in terms of volume and design, such as e.g. mobile or stationary as well as rigid tanks or flexible bags, can advantageously be introduced into the mixing circuit because the mounting of measuring devices on said containers can be dispensed with.

More complicated metering devices which are suited for variable filling volumes and are combined with the finished solution container/tank are e.g. associated with weighing techniques, continuous constant filling-level measurements, such as e.g. pressure measurement technique, echo sounding, or volumetric metering processes, e.g. balance chambers, and other methods that are not listed there.

Alternatively, depending on costs or safety aspects, the above-mentioned configurations of a metering device may be used.

To improve hygiene and sterility of the supplied liquid, a combination of an RO (reverse osmosis) with the mixing unit is advantageously provided. Moreover, the purity of the RO-produced liquid can be improved via further additional filter stages, such as deionization and/or sterile filtration, with respect to conductivity and microbiology in such a manner that an equally good or even better water quality, as is stipulated for the production of drugs, can be achieved.

If a temperature-controlled liquid is to be used, or if the dissolution times are to be reduced, a heater which is optionally provided can be used. Moreover, a static mixer may be used in support of the dissolution of the feedstock.

The mixing quality is microbially without residues; the device works in an energy-saving manner. Since the feedstock is validated, i.e. it is a medical product, and since the supplied liquid complies in terms of purity and exactness of the volume with the accuracy requirements, complicated in-house controls can be dispensed with.

It is possible to produce highly sterile drugs by adding further filter stages.

Figure 2:
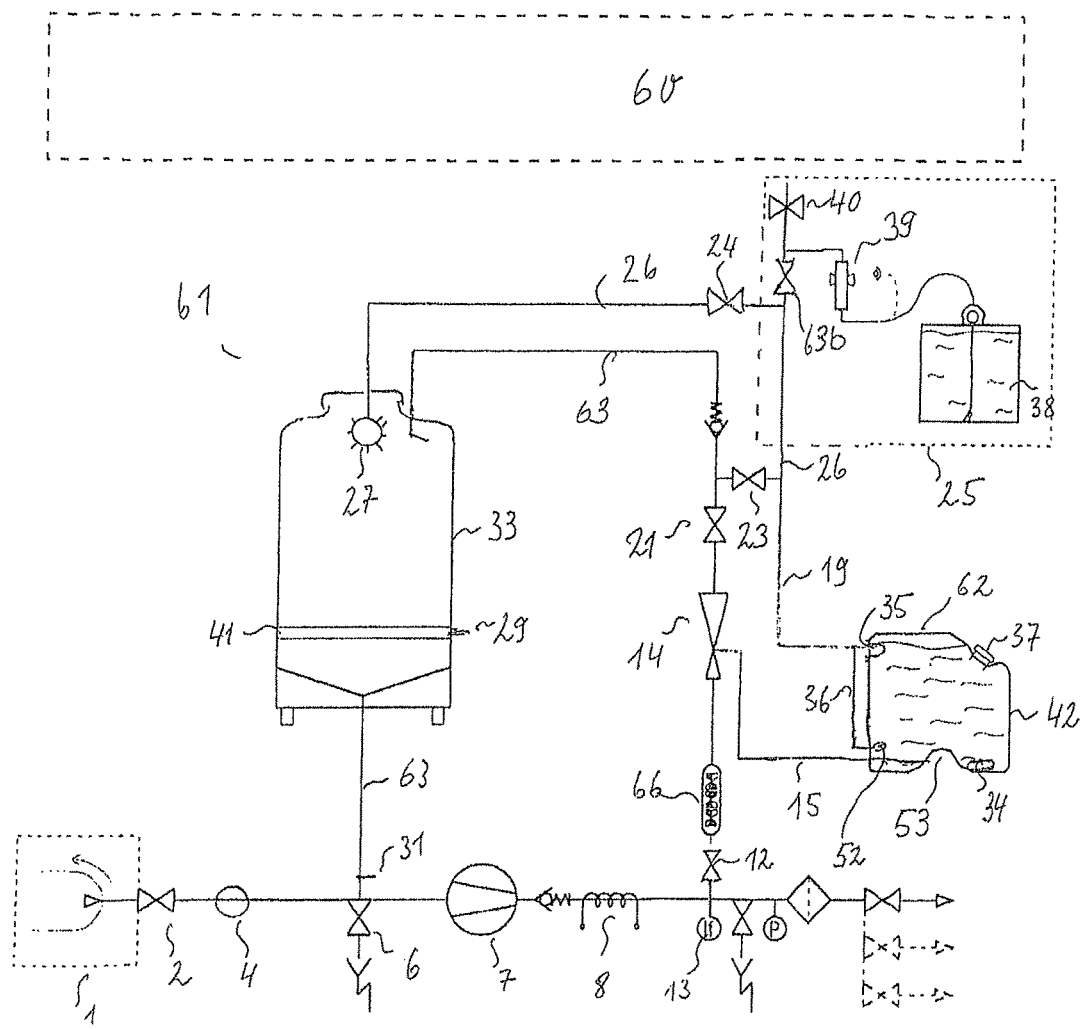
Figure 3:
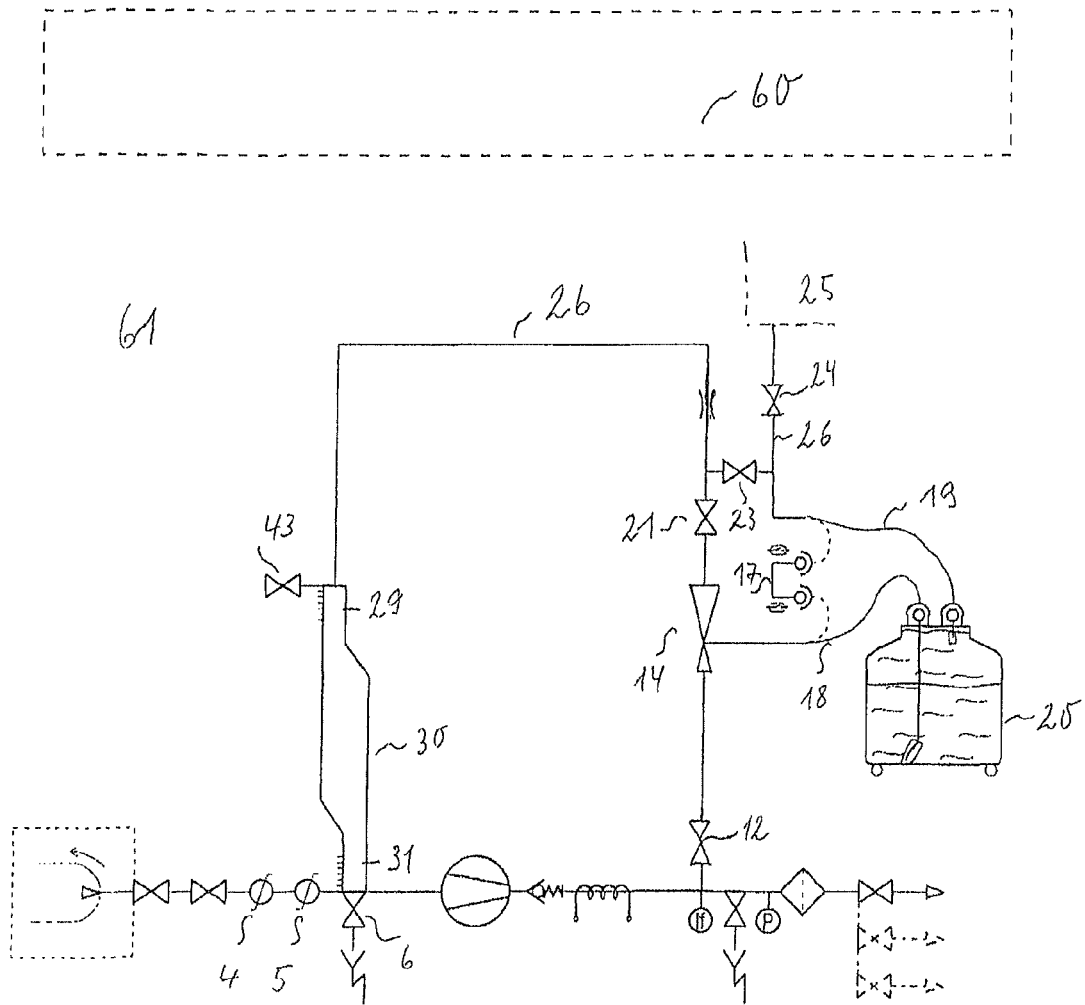
Figure 4:
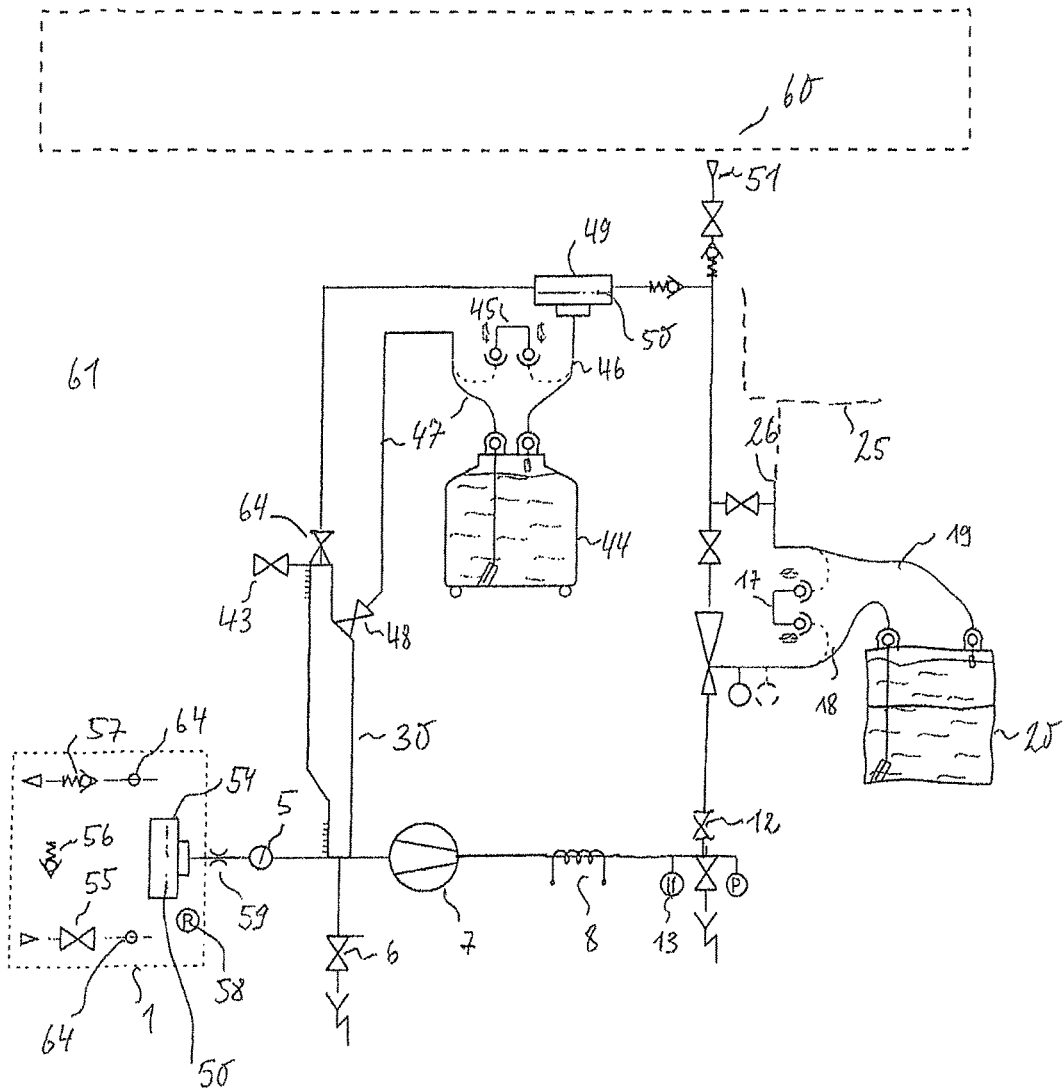

Embodiments of the invention will be described in more detail hereinafter with reference to the drawings. They show in FIG. 1 a device for mixing a feedstock in an exchangeable container and a finished solution container;

FIG. 2 a device for mixing a feedstock in an exchangeable container, which can be filled on site, and in a finished solution container with level markings and a disinfection/acid device;

FIG. 3 a device for mixing a feedstock in a feedstock container/bag without a finished solution container;

FIG. 4 a device for mixing a feedstock in a bag, a mobile finished solution container, sterile liquid supply, and additional sterile filtration.

FIG. 1 shows the liquid supply (1) and the failsafe metering which consists of the components operation valve (2), protection valve (3), operation flowmeter (4), protection system flowmeter (5) and the level sensors (31/29). Advantageously, the valves (2/3) are used in different types, e.g. membrane valve and/or a servo valve, to prevent failure or an unintended metering. The two flowmeters (4/5) are checked by the computer (60) of the mixing unit (61) and are verified through the volume, which is presupposed to be known, between the level sensors (29/31).

The optional measuring chamber (30) with known volume can here verify the flowmeters (4/5) independently of the tank. When a measuring chamber (30) is used, the level sensor (29) is also mounted thereon.

The finished solution container (preparation container) (33) is filled via the fill line (63) and upon use of a measuring chamber (30) via said chamber until the necessary volume is reached. The level sensor (31) is here preferably positioned in a vertical line section between tank outlet and outflow valve (6). The finished solution container (33) is vented via the hydrophilic vent filter (28). Overflow can be detected with leakage detector (32).

An emptying option for the finished solution container (33) is provided via the outflow valve (6) which for reasons of back-contamination should terminate downstream in a free outlet. This route is preferably chosen after a flushing operation or as a discarding possibility in case of a faulty finished solution. Advantageously, at the beginning of the filling process a part of the supplied liquid is first of all discarded via outflow valve (6) for preventing the influx of bacteria.

The inflow to the finished solution container (33) can also take place via the flowmeters from above into the container. Nevertheless, the position of the level sensors (29/31) remains downstream of the tank outlet/fill line (63).

At the beginning of the mixing process the pump (7) conveys part of the previously metered liquid out of the finished solution container (33) via the optional heater (8) and the optional static mixer (66) (FIG. 2), the optional conductivity/temperature measurement (13), the auxiliary fill valve (12), the venturi (14) into the feedstock container (20); in this case the mixing valve (21) and the flush valve (24) remain closed. The liquid feedstock mixture is circulating via the opened secondary mixing valve (23) and the mixing line (63) into the finished solution container (33). The flow direction in the feedstock container (20) can be reversed for a better dissolution of the feedstock by additionally opening mixing valve (21). Venturi (14) is here sucking the liquid feedstock mixture via the connection hose (18) out of the feedstock container (20). Due to a dynamic pressure produced by the throttle (22), liquid is flowing from above via connection hose (19) into the feedstock container (20). By extension of the connection (19) in the container (20), air can additionally be introduced from above into the container (20) by alternatingly switching the valves (23/24) in order to accelerate the dissolution process of the feedstock.

For emptying purposes the venturi (14) sucks the dissolved mixture out of the container (20) via the connection hose (18) in the opened state of the valve (24) until the optional empty-state detection (16) terminates the process. As a rule, the sucking off of the liquid feedstock mixture is time-controlled. Subsequently, the hoses (18/19) can be connected back to the parking station (17).

Pressure sensor (9) serves to monitor the pressure of the feedstock container (20); said sensor may also be mounted at another place (here not shown) of the hydraulic circuit. The pressure sensor (9) can also check the tightness of the connected components, such as e.g. transfer filter (11), transfer valve (10).

The finished solution is pumped out of the finished solution tank (33) by means of the pump (7) and the transfer valve (10) and the transfer filter (11) to the place of use or into the provided tank.

The mixing unit (61) is alternatingly flushed such that liquid flows through all lines (26/63), the cleaning spray head (27) being mounted such that the whole inner surface of the finished solution container (33) can be sprayed.

To improve the cleaning efficiency, a cleaning/disinfecting device (25) may optionally be installed in the line (26) leading to the finished solution container (33). To check the concentration of both the finished mixture and a disinfection solution, the conductivity measurement (13) may be employed.

FIG. 2 shows a simplified metering device which consists as a rule of an inlet valve (2), a flowmeter or water meter (4) and the level sensors (31/29). In the simplest case it is also possible to perform metering without flowmeter (4) because the accuracy of the supplied volume can be controlled by the level sensor (29) and also as the fill height by means of a translucent portion or a surrounding tank marking by the user. A possible faulty inclined position of the tank that is of relevance to the volume can thereby also be detected.

Optionally, the software of the computer (60) is equipped such that a defective open valve (6) is monitored by means of level sensor (31), and leaky defective valves or connections (10; 11; 12) are detected by means of pressure holding test by the pressure sensor (9).

To compensate for an inclined position of the tank, use can be made of a solution (not shown here), such as e.g. adjustable base, or a comparable solution. To avoid tank bulges which are caused by age or load and are of relevance to the volume, the tank (33) may be provided in the center with a dimensionally stable tank belt. The above-mentioned metering is only suited for fixed inlet levels. According to the invention also plural surrounding level monitoring markings (41) are mounted, and a level sensor (29) for each desired volume to be metered.

The container (41) is a refillable feedstock container with a straight, inclined or conical or dented bottom and a lower tangential inflow (34) which, when viewed from the front, is arranged at the bottom at the right side with a large diameter, e.g. 32 mm.

The container comprises an upper tangential outlet (35) which, when viewed from the front, is arranged at the left side at the top and has a diameter of e.g. 15 mm, and comprises a further lower tangential outlet (52) which, when viewed from the front, is arranged at the bottom at the left side and has a diameter of e.g. 20 mm. The container (42) includes a closeable lid (37) which is arranged in a funnel-shaped indentation so as to fill, on the one hand, the free space of the paraboloid of revolution during the mixing process in the container and to permit, on the other hand, the supply of salt without any spilling.

The lower optional outflow (52) serves the additional discharge of the filled-in feedstock at small flow rates through the container (42) at the beginning of the mixing operation, e.g. during lumping, and is arranged on the outer wall of the container (42) such that it terminates at the upper end in the outlet (35). To simplify the salt supply in the opened state of the lid (37), the container is provided with an upper bag tray (62), which is configured as a platform. A barcode reader for verifying the feedstock can be connected to the computer (60) of the mixing unit (61).

Furthermore, FIG. 2 shows a chemical metering/cleaning device (25). In the opened state of valve (63) and in the closed state of valves (24/40/23), disinfecting/cleaning agent can be sucked by means of venturi (14) out of the canister (38) until the conductivity/temperature sensor (13) records the desired target conductivity. The level monitoring chamber (39) can act as an empty-state detector for the canister (38) and also as a protection system with respect to undesired sucking. Since the valve (40) is open in the inoperative state, the level-monitored chamber (39) has to be empty.

With the device (25) the safe metering of critical liquid substances, such as acetic acid, is also possible for the production of HD concentrates if this feedstock has to be introduced separately.

Instead of a chemical cleaning device (25), an equivalent physical cleaning device (25) used for disinfection and provided with an ozone cell would also be possible.

Likewise, a thermal disinfection or a combination of thermal and chemical disinfection by means of the heater (8) is possible.

FIG. 3 shows a mixing device without a preparation tank. The flowmeters (4/5) are here verified via the measuring chamber (30). The filling of the feedstock container (20) is performed via the line (26), the valve (21) via the venturi (14), the hose (18) or alternatingly the valve (23) and the hose (19) into the feedstock container (20), which is filled only partly with feedstock (21), so as to accommodate the additional amount of liquid needed for dilution.

The mixing process is carried out in the way as has already been described in FIG. 1. To improve the mixing efficiency, a static mixer (66) as shown in FIG. 2 can also be used here.

Advantageously, the feedstock container (20) is here mobile and can be moved as a finished solution container to the place of use after the mixing operation has been performed. Likewise, a transfer as described in FIG. 1 is also possible.

In the case of a stationary feedstock tank (20) it is possible to configure the mixing unit (61) such that it is mobile.

The measuring chamber is subdivided into three sections with a middle part of a larger volume and with two routes having smaller cross-sections. The two end sections serve the finer dissolution, and the fill level can there be determined either as a transparent measurement route optically or also capacitively by means of level sensors (29/31) or with another sensor technique by the computer (60) of the mixing unit (61). The value or also the values output by the flowmeters are compared or verified with the volume of the measuring chamber (30) which is presupposed to be known. The measuring chamber (30) may also have constructionally different geometrical shapes. The valve (43) serves the ventilation of the measuring chamber (30) so as to empty the same, e.g. before the beginning of a measurement, via the outflow valve (6).

FIG. 4 shows the use of a mixing device with a sterile liquid supply connection (1), the liquid of an upstream, here only partly shown, reverse osmosis (RO) being introduced via the input filter (54) to the measuring chamber (30).

The flowmeters (64), which are symbolically shown as an integral part of a reverse osmosis system, serve as operation flowmeters and the flowmeter (5) as a protection system flowmeter. The valve (55), also an integral part of a reverse osmosis system, serves as a protection valve for a faulty metering operation; in this case, too, the reverse osmosis system can be switched off. The position of the illustrated flow sensors is possible within the RO also at other places serving the functional purpose. Instead of an RO, the use of a liquid provided in a tank with pressure raising system is also possible.

For the validation of the input filter (54) compressed air can be conveyed by means of air connection (51) to the secondary side of the input filter and the liquid can be displaced out of the secondary chamber. In the case of an intact input filter membrane (50), a pressure drop cannot be recorded by the pressure sensor (58) because the intact membrane (50) has an air-impermeable function.

FIG. 4 also shows an additional fill filter (49) which can also be designed as a sterile filter. The supplied liquid is introduced via the filter membrane (50) and the fill connection (46) in a liquid-calmed manner into the fill container (44). Circulation takes place via the line (47), the valve (48) and the pump (7).

With the help of the optional heater (8) and the measuring device (13) the finished solution can be adjusted to a desired temperature and concentration. The computer (60) of the mixing unit (61) also offers the possibility of recording the used feedstocks and the produced product, respectively, e.g. by means of barcode reader and connected printer. For reasons of simple handling the lines (18,19/46,47) can here respectively be combined into a twin hose with a respective coupling. After the mixing operation has been completed and the feedstock container (20) has been emptied, the container is disposed of. The hoses (18, 19) are plugged back onto the parking station (17) and the hoses and couplings (46, 47), respectively, onto the parking station (45). Subsequently, the mixing unit (61) is again ready for operation and can be flushed and/or disinfected. The finished solution container (44) can be moved to the place of use and can there be processed near the patient preferably by means of air pressure at the coupling place (46) and a disposable item with filter at the coupling place (47). The filters (49/54) are advantageously configured as sterile filters; as has already been described, the membrane validation can be carried out by means of air pressure.

The invention claimed is:

1. A mixing device for producing ready-to-use medical flush solutions comprising:
   - a finished solution container initially contains a liquid, the liquid is an ultrapure water,
   - a feedstock container initially contains a powdery and/or granulated and/or slurried feedstock,
   - a pump,
   - a venturi with a convergence chamber and a divergence chamber,
   - a first mixing valve,
   - a secondary mixing valve,
   - a computer,
   - a recirculating circuit circulates the liquid from finished solution container through the pump, the convergence chamber, the feedstock container, the secondary mixing valve, and returns to the finished solution container,
   - a secondary circuit circulates the liquid from the finished solution container through the pump, the venturi which pulls feedstock from the feedstock container, the first mixing valve, the secondary mixing valve, the feedstock container, and returns to the finished solution container,
   - where the liquid and the feedstock are mixed in either the recirculating circuit or the secondary circuit.

2. The mixing device of claim 1 further comprising a throttle upstream of the venturi.

3. The mixing device of claim 1 wherein the feedstock container is refillable.

4. The mixing device of claim 1 further comprising at least one flow meter in the recirculating circuit and connected to the computer.

5. The mixing device of claim 4 further comprising two flow meters in the recirculating circuit and connected to the computer.

6. The mixing device of claim 1 further comprising a transfer line branching off the recirculating circuit.

7. The mixing device of claim 1 wherein the medical flush solutions being hemodialysis concentrates.

8. The mixing device of claim 1 wherein the computer monitors the mixing device.

* * * * *